(12) United States Patent
Kapadia et al.

(10) Patent No.: US 11,246,673 B2
(45) Date of Patent: Feb. 15, 2022

(54) STERILE BARRIER ASSEMBLY FOR USE IN ROBOTIC SURGICAL SYSTEM

(71) Applicant: Covidien LP, Mansfield, MA (US)

(72) Inventors: Jaimeen Kapadia, Cambridge, MA (US); Brian Rockrohr, Guilford, CT (US)

(73) Assignee: Covidien LP, Mansfield, MA (US)

( * ) Notice: Subject to any disclaimer, the term of this patent is extended or adjusted under 35 U.S.C. 154(b) by 314 days.

(21) Appl. No.: 15/527,877

(22) PCT Filed: Nov. 13, 2015

(86) PCT No.: PCT/US2015/060498
§ 371 (c)(1),
(2) Date: May 18, 2017

(87) PCT Pub. No.: WO2016/081286
PCT Pub. Date: May 26, 2016

(65) Prior Publication Data
US 2018/0325616 A1 Nov. 15, 2018

Related U.S. Application Data

(60) Provisional application No. 62/081,172, filed on Nov. 18, 2014.

(51) Int. Cl.
*A61B 46/10* (2016.01)
*A61B 34/30* (2016.01)
*A61B 46/00* (2016.01)

(52) U.S. Cl.
CPC .............. *A61B 46/10* (2016.02); *A61B 34/30* (2016.02); *A61B 46/00* (2016.02)

(58) Field of Classification Search
CPC .......... A61B 46/10; A61B 34/30; A61B 46/00
See application file for complete search history.

(56) References Cited

U.S. PATENT DOCUMENTS 5,630,782 A    5/1997 Adair
5,772,628 A *  6/1998 Bacich ............... A61B 17/3417
                                                   604/43

(Continued)

FOREIGN PATENT DOCUMENTS

WO       2010121117 A1    10/2010
WO    WO 2011-037394       3/2011

(Continued)

OTHER PUBLICATIONS

International Search Report for (PCT/US2015/060498) date of completion is Feb. 29, 2016 (7 pages).

(Continued)

*Primary Examiner* — Lynsey C Eiseman
*Assistant Examiner* — Jessandra F Hough
(74) *Attorney, Agent, or Firm* — Carter, DeLuca & Farrell LLP (57) ABSTRACT

A sterile barrier assembly includes a tab sliding along a sliding path in a cavity of the sterile barrier assembly and a barrier membrane partitioning the cavity into a sterile side and a non-sterile side. The barrier membrane moves with the tab as the tab slides along the sliding path. A first portion of the tab interfaces with an output of a surgical tool driving unit on the non-sterile side. A second portion of the tab interfaces with a tool driver of a surgical tool on the sterile side.

10 Claims, 8 Drawing Sheets

(56) References Cited

U.S. PATENT DOCUMENTS

| | | | | |
|---|---|---|---|---|
| 6,132,368 | A | * | 10/2000 | Cooper .................. A61B 46/13 600/102 |
| 7,044,940 | B1 | * | 5/2006 | Hahn ....................... A61C 5/66 206/363 |
| 7,158,860 | B2 | | 1/2007 | Wang et al. |
| 7,752,920 | B2 | | 7/2010 | Blumenkranz et al. |
| 8,375,808 | B2 | | 2/2013 | Blumenkranz et al. |
| 9,469,034 | B2 | | 10/2016 | Diolaiti et al. |
| 2004/0049205 | A1 | | 3/2004 | Lee et al. |
| 2006/0235436 | A1 | | 10/2006 | Anderson et al. |
| 2009/0248039 | A1 | * | 10/2009 | Cooper .................. A61B 34/71 606/130 |
| 2009/0287223 | A1 | | 11/2009 | Pua et al. |
| 2010/0292707 | A1 | | 11/2010 | Ortmaier et al. |
| 2013/0172713 | A1 | | 7/2013 | Kirschenman |
| 2013/0247921 | A1 | * | 9/2013 | Dye ....................... A61B 46/23 128/853 |

FOREIGN PATENT DOCUMENTS

| | | |
|---|---|---|
| WO | WO 2012-044869 | 6/2012 |
| WO | 2014005689 A2 | 1/2014 |
| WO | 2017015167 A1 | 1/2017 |

OTHER PUBLICATIONS

Extended European Search Report issued in European Application No. 15861501.3 dated Jun. 18, 2018.

Chinese Office Action dated Mar. 25, 2019 issued in Chinese Application No. 201580061785.6.

Examination Report issued in European Patent Application No. 15861501.3, dated Jun. 8, 2021.

* cited by examiner

STERILE BARRIER ASSEMBLY FOR USE IN ROBOTIC SURGICAL SYSTEM

CROSS-REFERENCE TO RELATED APPLICATIONS

This application is a U.S. National Stage Application filed under 35 U.S.C. § 371(a) of International Patent Application No. PCT/US2015/060498, filed Nov. 13, 2015, which claims the benefit of and priority to U.S. Provisional Patent Application No. 62/081,172, filed Nov. 18, 2014, the entire disclosure of which is incorporated by reference herein.

BACKGROUND

Robotic surgical systems have been used in minimally invasive medical procedures. Some robotic surgical systems include a console supporting a robot arm and a surgical instrument that is mounted to the robot arm. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument.

The utilization is subject to strict sterility requirements. Current sterilization techniques (such as steam sterilizing) are not suitable or only conditionally suitable for electrical and electronic equipment. In order to achieve sterility nevertheless, sterile plastic or rubber covers, so-called sterile barriers, are generally pulled over the (inherently non-sterile) device, or are used to give the device a sterile covering.

Therefore, there is a need for a sterile barrier assembly that provides for an easier removal and attachment to a surgical instrument.

SUMMARY

In accordance with an embodiment of the present disclosure, there is provided a sterile barrier assembly including a tab sliding along a sliding path in a cavity of the sterile barrier assembly and a barrier membrane partitioning the cavity into a sterile side and a non-sterile side. The barrier membrane at least partially moves with the tab as the tab slides along the sliding path. A first portion of the tab interfaces with an output of a surgical tool driving unit on the non-sterile side. A second portion of the tab interfaces with a tool driver of a surgical tool on the sterile side.

In an embodiment, the barrier membrane may be interposed between the first and the second portions of the tab.

In another embodiment, the barrier membrane may be adjacent the first portion of the tab and the barrier membrane may contour around at least one of the first portion of the tab and the surgical tool driving unit output as the first portion of the tab interfaces with the surgical tool driving unit output. Alternatively, the barrier membrane may be adjacent the second portion of the tab and the barrier membrane may contour around at least one of the second portion of the tab and the tool driver as the second portion of the tab interfaces with the tool driver. The surgical tool driving unit output may move rotationally while the tab and the tool driver move translationally, and the tab may impart translational movement to the tool driver from the rotational output of the driving unit.

In yet another embodiment, the sterile barrier assembly may further include an elongated element attached to the tab and extending into a longitudinal channel in the sterile barrier assembly. The tab and elongated element may slide in a longitudinal direction of the channel. In addition, the tab may slide longitudinally along a guide rail in the sterile barrier assembly.

In still another embodiment, the barrier membrane may be formed of an elastic material. Alternatively, the barrier membrane may be formed of an inelastic material. In particular, the barrier membrane may include slack in the inelastic material that tautens as the tab slides in at least one direction. The barrier membrane may be hermetically sealed to at least one component of the sterile barrier assembly.

In accordance with another embodiment of the present disclosure, there is provided a robotic surgical system including a sterile instrument, a manipulator assembly, a non-sterile drive unit, and a sterile barrier. The sterile instrument has a surgical tool manipulated by a plurality of tool drivers in a plurality of directions. The manipulator assembly has a linkage coupling a base to an instrument holder supporting the sterile instrument. The linkage is movable in a plurality of degrees of freedom. The non-sterile drive unit includes a plurality of driven outputs. The sterile barrier has a barrier membrane partitioning the sterile barrier into a sterile side coupled to the sterile instrument and a non-sterile side coupled to the non-sterile drive unit. The barrier membrane at least partially moves with a plurality of tabs in the sterile barrier as the tabs slide along respective tab sliding paths. The tabs couple the driven outputs of the drive unit to the tool drivers of the sterile instrument.

In an embodiment, the tabs may include a first portion coupling to the driven outputs of the drive unit and a second portion coupling to the tool drivers of the instrument. The barrier membrane may be interposed between the first and second portions. At least one portion of each tab may be slidingly attached to at least one guide rail. The at least one guide rail may define the respective tab sliding paths for each tab. An axial translation of each tab along the at least one guide rail may impart a translational movement to the respective tool drivers of the instrument. The barrier membrane may be formed of polyethylene or polycarbonate.

In accordance with another aspect of the present disclosure, there is provided a method including actuating a driven output of an instrument drive unit detachably coupled to a non-sterile side of a sterile barrier having a barrier membrane partitioning the non-sterile side of the sterile barrier from a sterile side; responsive to the actuating, sliding a tab in the sterile barrier detachably coupled to the driven output along a translational tab slide path in the sterile barrier; at least partially moving the barrier membrane as the tab slides along the translational tab slide path; responsive to the sliding of the tab, translationally moving a driver of a sterile instrument detachably coupled to the sliding tab on the sterile side of the sterile barrier; and manipulating a surgical tool connected to the driver as the driver is translationally moved.

DESCRIPTION OF THE DRAWINGS

Various embodiments of the present disclosure are described hereinbelow with reference to the drawings, wherein.

DETAILED DESCRIPTION

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
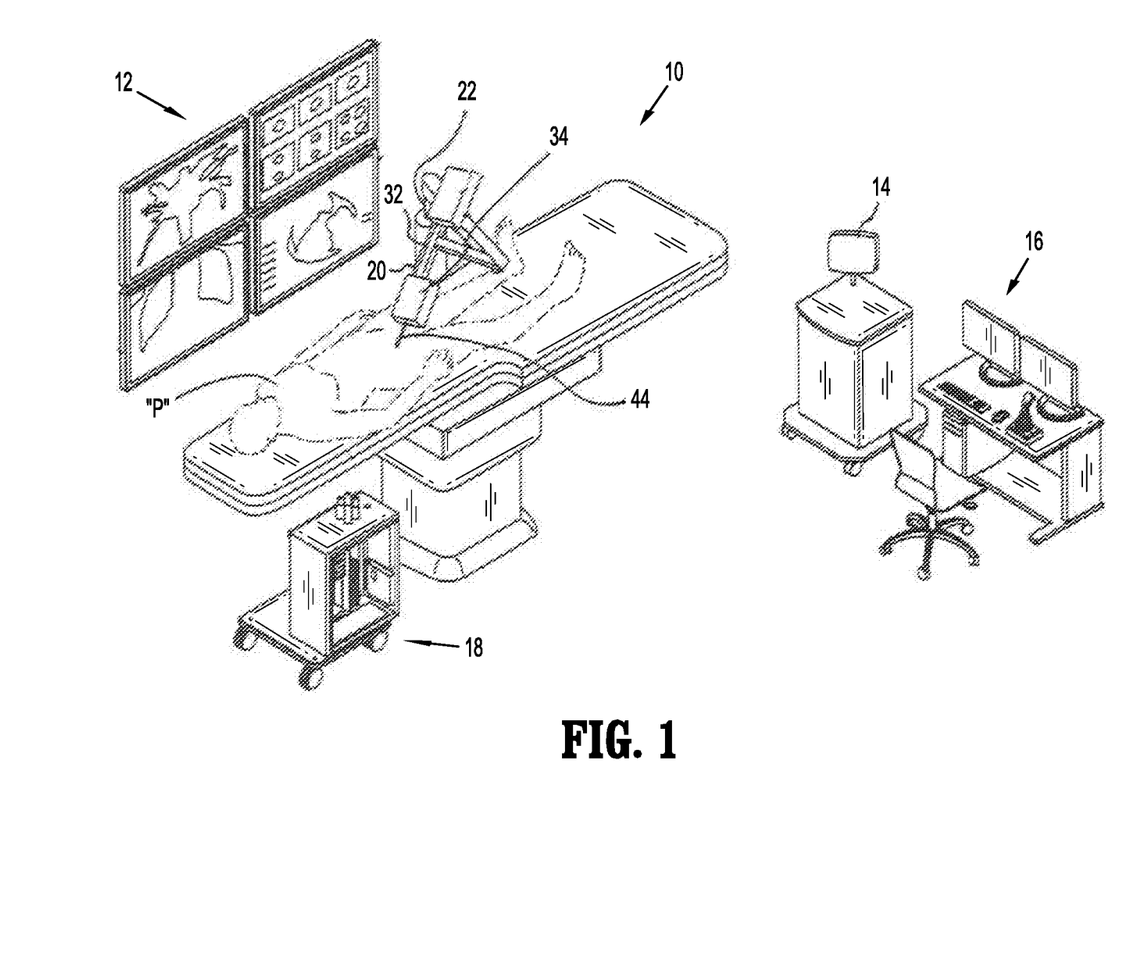
FIG. 1 is a perspective view of a robotic surgical system.

With reference to FIG. 1, there is provided a robotic surgical system 10 including a sterile barrier assembly 100 (FIG. 5) in accordance with an embodiment of the present disclosure. Robotic surgical system 10 generally includes displays 12, a mapping system 14, an input control system 16, an electronic control system 18, a manipulator assembly 20, and a manipulator assembly support structure 22. In particular, mapping system 14 determines a position and orientation of a sensor-equipped surgical instrument 44. Input control system 16 controls actuation of surgical instrument 44 through user input. Electronic control system 18 translates user input from input control system 16 into actuation control signals. In response to the actuation control signals, manipulator assembly 20 actuates surgical instrument 44. Manipulator assembly 20 includes a translation assembly 32 and a drive assembly 34 mounted on translation assembly 32. Drive assembly 34 is configured to actuate the surgical instrument 44 in response to the actuation control signals from electronic control system 18. Manipulator assembly support structure 22 is utilized to position manipulator assembly 20 in proximity to a patient "P".

Figure 2:
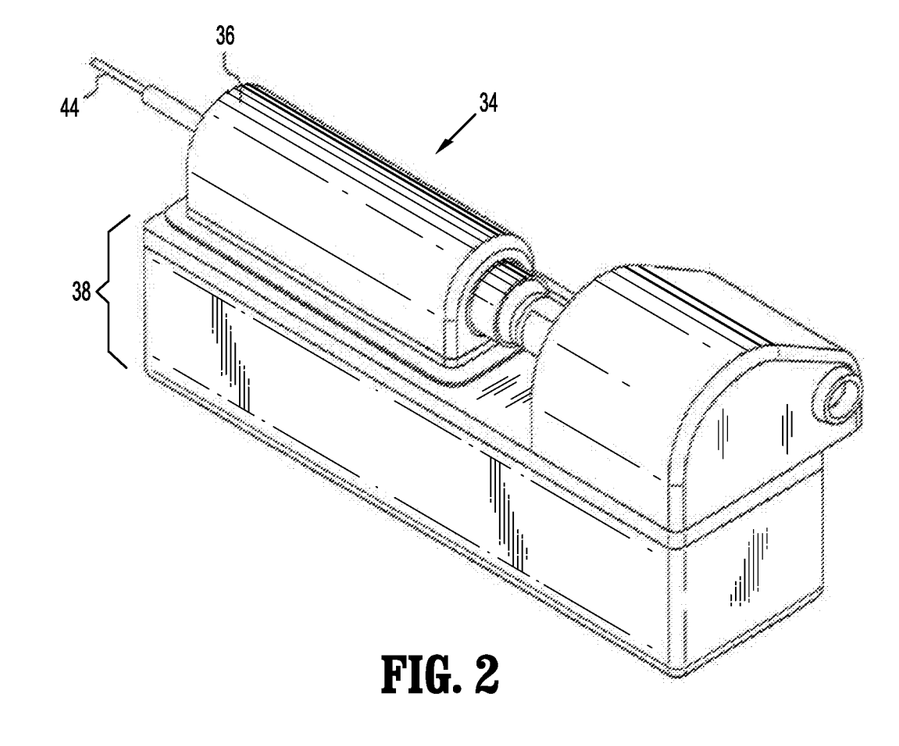
FIG. 2 is a perspective view of a drive assembly of the robotic surgical system of FIG. 1.
Figure 3:
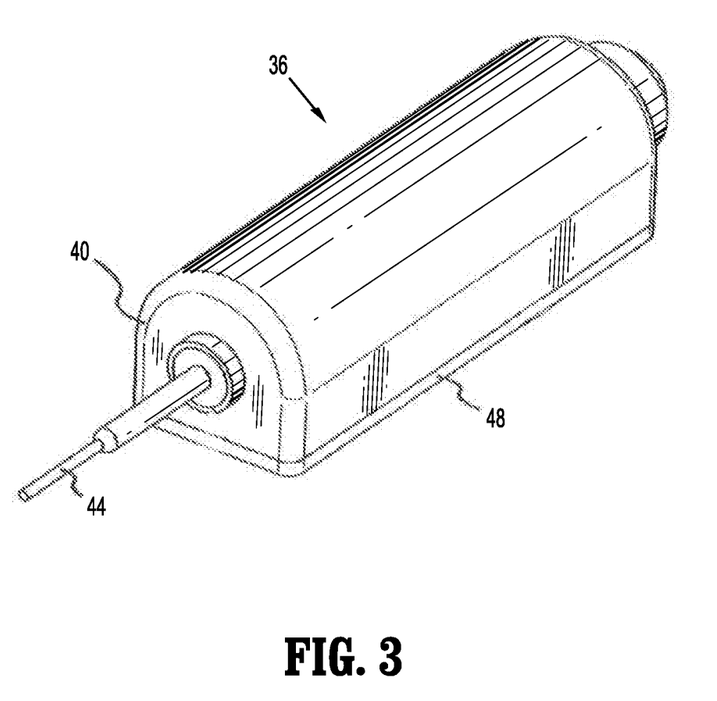
FIG. 3 is a perspective view of a medical device cartridge of the drive assembly of FIG. 2.
Figure 4:
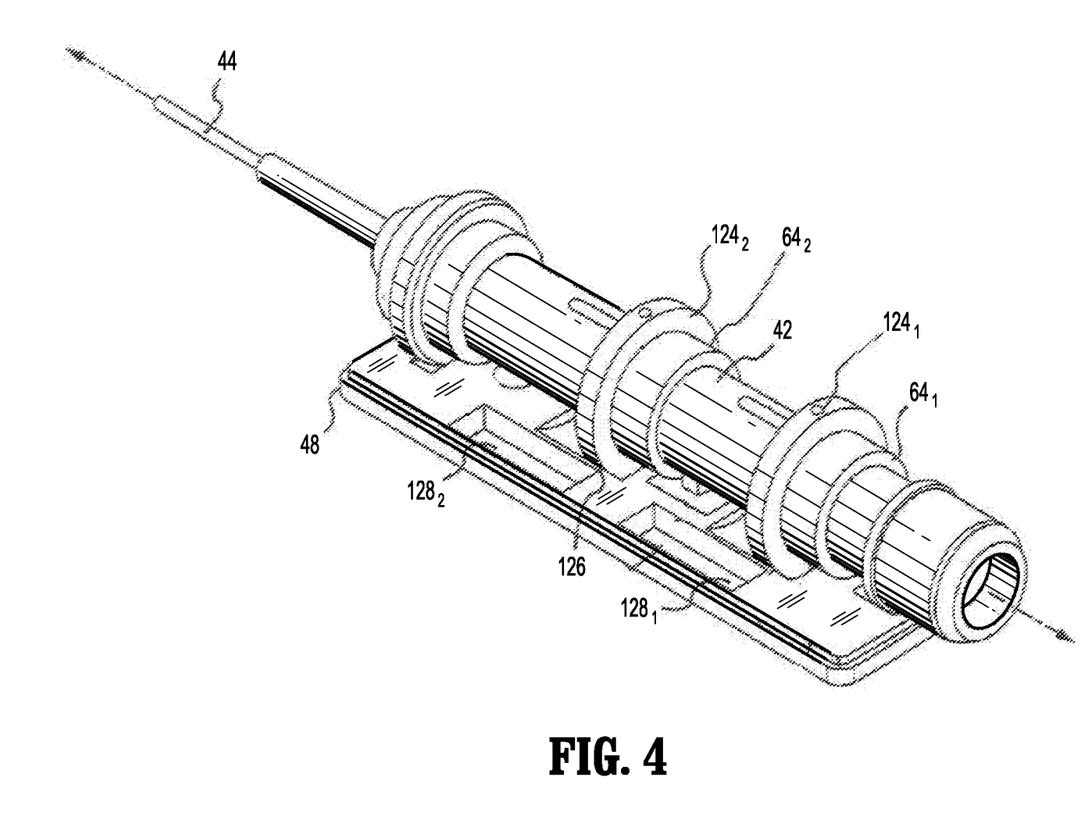
FIG. 4 is a perspective view of the medical device cartridge of FIG. 3, with an outer housing removed therefrom.

With reference now to FIGS. 2-4, drive assembly 34 includes an instrument drive unit ("IDU") 38 and a medical device cartridge 36 removably attached to IDU 38. Medical device cartridge 36 includes an outer housing 40 (FIG. 3), a base portion 48 (FIG. 3), and a rotatable assembly 42 (FIG. 4) disposed within outer housing 40. Rotatable assembly 42 includes surgical instrument 44 operatively coupled thereto. Rotatable assembly 42 includes mechanical drive interfaces $64_{1,2}$ operatively associated with tabs $176_{1,2}$ (FIG. 5) of sterile barrier assembly 100 (FIG. 5).

Figures 5, 6:
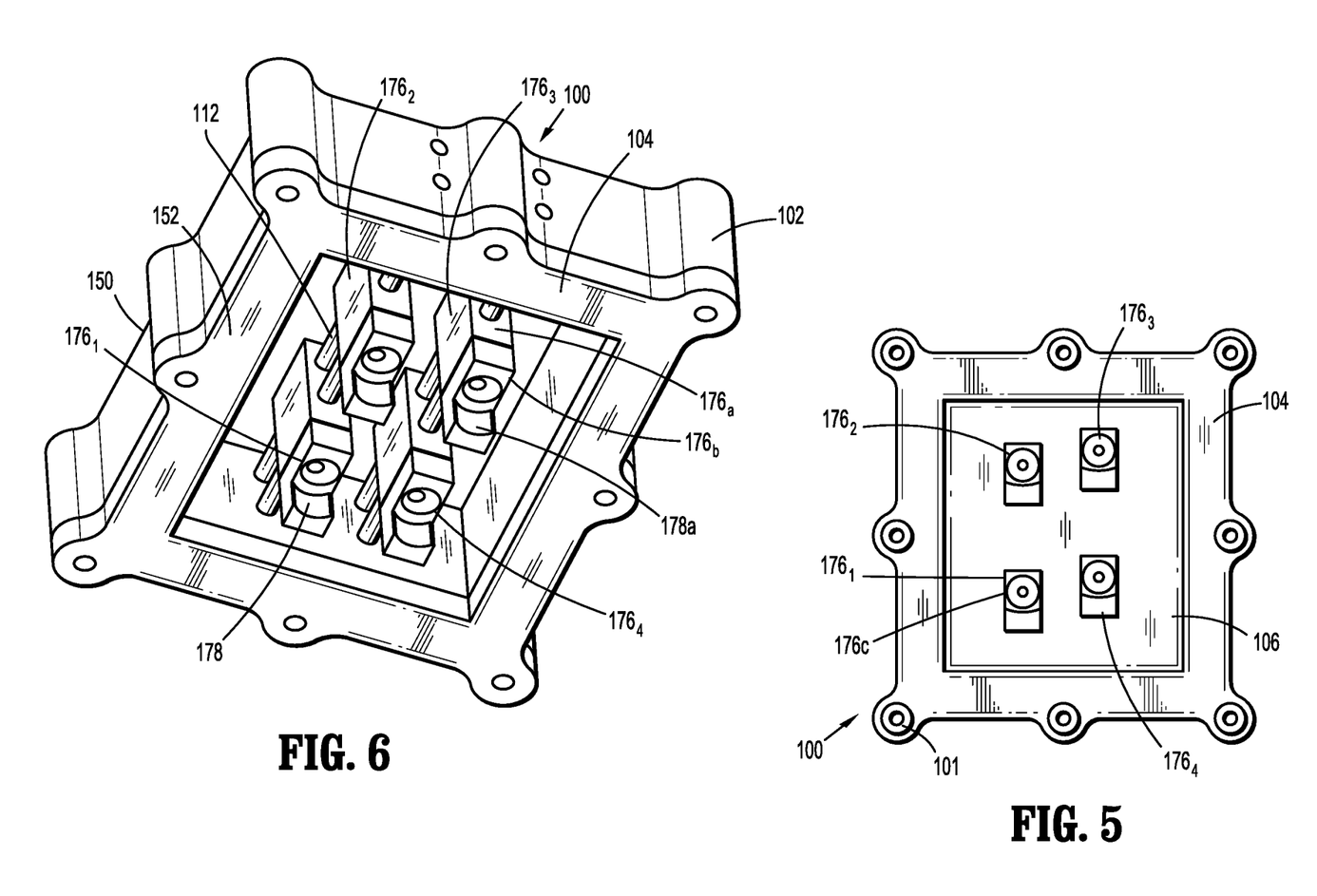
FIG. 5 is a top view of a sterile barrier assembly for use with the robotic surgical system of FIG. 1 in accordance with an embodiment of the present disclosure.
FIG. 6 is a perspective view of the sterile barrier assembly of FIG. 5, with a barrier membrane removed therefrom.

With reference now to FIG. 6, sterile barrier assembly 100 in accordance with an embodiment of the present disclosure is configured to separate a sterile portion of surgical instrument 44 with the non-sterile portion of manipulator assembly 20 (FIG. 1), while enabling motion to pass from IDU 38 (FIG. 2) to surgical instrument 44. Sterile barrier assembly 100 includes a base member 102, a securing member 104, a barrier membrane 106 (FIG. 5), actuation rails 112, and tabs $176_{1-4}$. Base member 102 and securing member 104 define a cavity 108 dimensioned to receive actuation rails 112 and tabs $176_{1-4}$ operatively mounted on actuation rails 112.

With reference now to FIG. 5, barrier membrane 106 is securely interposed between base member 102 and securing member 104 such that barrier membrane 106 establishes a hermetic seal between the sterile portion of surgical instrument 44 and the non-sterile portion of manipulator assembly 20 (FIG. 1). For example, screws 101, rivets, welds, glue, or other fasteners may be used to secure barrier membrane 106 to a periphery of sterile barrier assembly 100. Moreover, barrier membrane 106 is also securely fixed to each tab $176_{1-4}$. For example, a screw 176c may be utilized to securely fix barrier membrane 106 to the respective tab $176_{1-4}$. Barrier membrane 106 may be formed of a thin elastic material such as, e.g., silicone rubber. In addition, barrier membrane 106 may be formed of other elastic or inelastic materials, e.g., polyethylene, latex, nitrile rubber, plastic, vinyl, or neoprene. In some instances, extra barrier membrane 106 may be provided within cavity 108, to provide slack in barrier membrane 106 between tabs $176_{1-4}$ and base and securing members 102, 104 to inhibit damage to barrier membrane 106 and undesirable pulling force applied to tabs $176_{1-4}$ by barrier membrane 106.

With reference back to FIG. 6, each tab $176_{1-4}$ includes a first portion 176a and a second portion 176b. Barrier membrane 106 is securely positioned between first and second tab portions 176a, 176b. Under such a configuration, first portion 176a of each tab $176_{1-4}$ is disposed on a non-sterile side 150 of sterile barrier assembly 100 and second portion 176b of each tab $176_{1-4}$ is disposed on a sterile side 152 of sterile barrier assembly 100. Tabs $176_{1-4}$ are free to move with respect to barrier membrane 106. Under such a configuration, tabs $176_{1-4}$ can transmit force and torque from IDU 38 to surgical instrument 44.

With continued reference to FIG. 6, second portion 176b of each tab $176_{1,2}$ includes an engaging portion 178 configured to engage a respective mechanical drive interface $64_{1,2}$ (FIG. 4) of medical device cartridge 36. Engaging portion 178 includes a finger 178a defining, e.g., a groove or concaved portion, adapted to facilitate engagement of tabs $176_{1,2}$ with respective mechanical drive interface $64_{1,2}$ (FIG. 4) of medical device cartridge 36.

Figure 7:
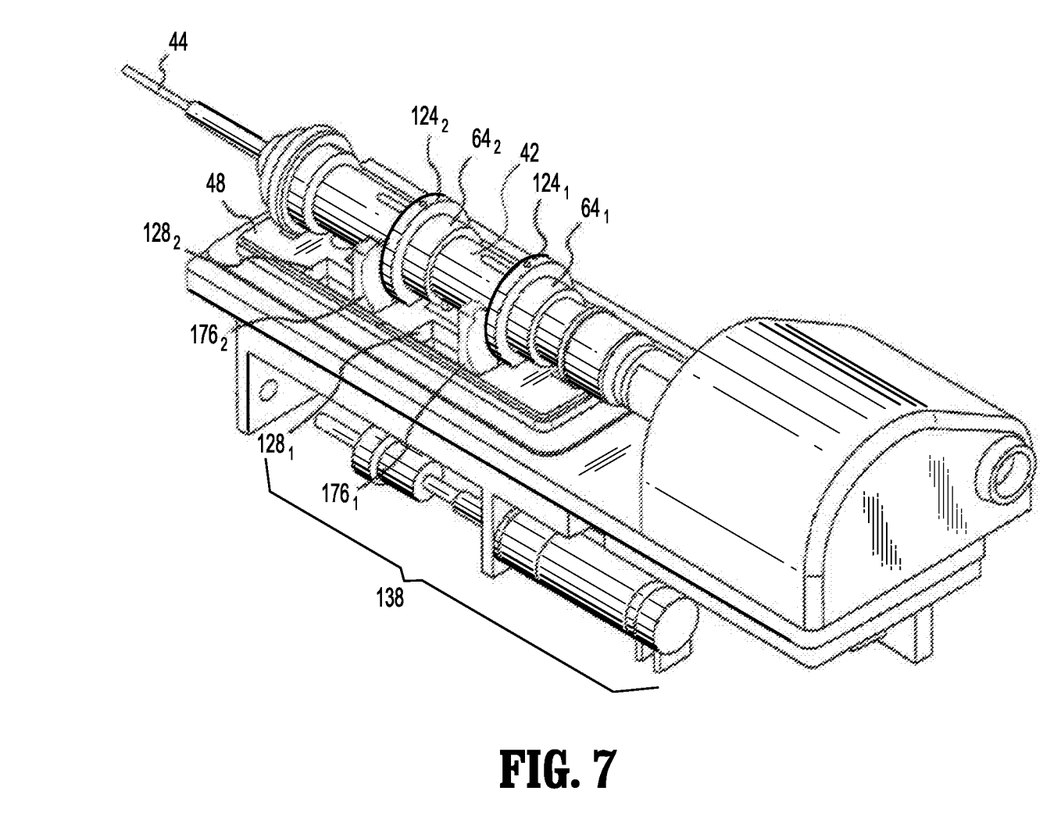
FIG. 7 is a perspective view of the drive assembly of FIG. 2, with portions of housings of a medical device cartridge and an instrument drive unit removed to show the drive assembly in greater detail.

With reference now to FIG. 7, first tab $176_1$ extends through slot $128_1$ defined in base portion 48 of medical device cartridge 36 and operatively engages flange $124_1$ of drive interface $64_1$. Second tab $176_2$ extends through slot $128_2$ in base portion 48 and operatively engages flange $124_2$ of drive interface $64_2$. IDU 38 includes a drive system 138 operatively coupled to first and second tabs $176_{1,2}$ to impart translational movement onto respective drive interfaces $64_{1,2}$ (FIG. 4) of medical device cartridge 36. IDU 38 further includes a dedicated motor controller (not shown) for drive system 138. Tabs $176_{1,2}$ are configured to be driven by a motor. As tabs $176_{1,2}$ are driven by the motor, tabs $176_{1,2}$ travel along actuation rail 112 (FIG. 6) and impart translational movement onto respective drive interfaces $64_{1,2}$ (FIG. 4). Motor controller communicates with electronic control system 18 and controls movement of the motor of drive system 138. While use of only first and second tabs $176_{1,2}$ have been shown, it is also contemplated that all four tabs $176_{1-4}$ may be utilized in other surgical instruments.

In addition, IDU 38 may include a force sensor (not shown), such as, for example a strain gauge, coupled to tab $176_{1,2}$. Strain gauge is configured to measure actuation forces being applied by drive system 138 to drive interfaces $64_{1,2}$. Strain gauge 190 is electrically coupled to motor controller and electronic control system 18 to communicate measured force being applied to the respective drive interface $64_{1,2}$. A force sensor ensures at least a minimum contact force between tab $176_{1-4}$ and respective drive interface $64_{1,2}$ is maintained. As discussed hereinabove, by providing slack in barrier membrane 106 between tabs $176_{1-4}$ and base and securing members 102, 104, undesirable pulling force, applied to tabs $176_{1-4}$ by barrier membrane 106, may be reduced. In this manner, more accurate readings by the force sensor may be achieved.

Figure 8:
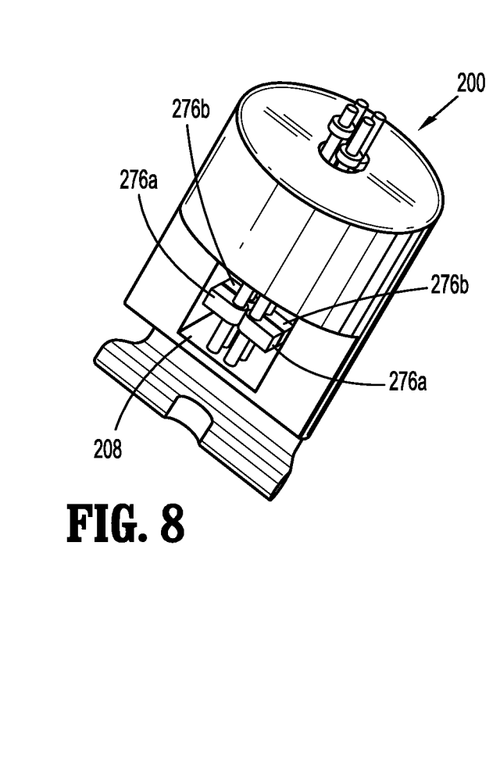
FIGS. 8-13 are perspective views of instrument drive units illustrating various tab arrangements.
Figure 9:
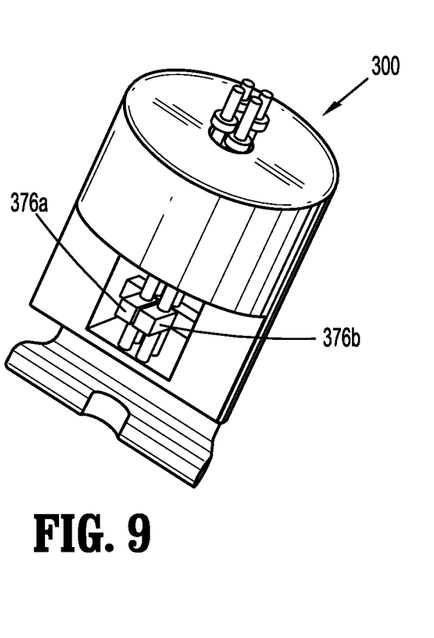
Figure 10:
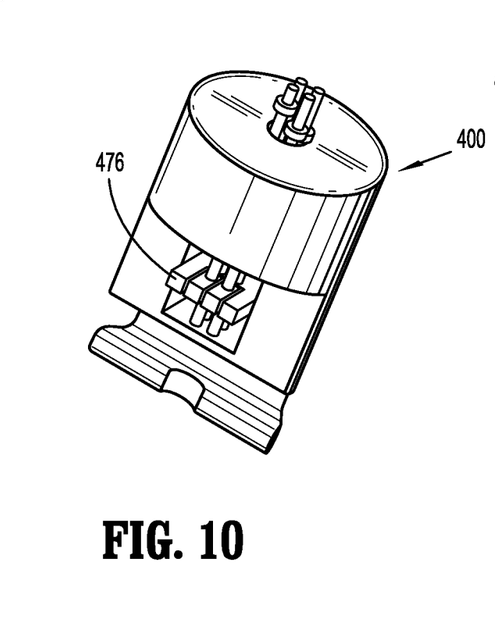

It is also contemplated that the barrier membrane configuration of sterile barrier assembly 100 may be utilized in various tab/rail configurations. With reference to FIG. 8, an IDU 200 includes four tabs $276_{a,b}$. A first pair of tabs $276_a$ is in a superposed relation with a second pair of tabs $276_b$. Each tab $276_{a,b}$ includes first and second portions (not shown). As discussed hereinabove, barrier membrane 106 may be interposed between first and second portions of first pair of tabs $276_a$ or second pair of tabs $276_b$. With reference to FIG. 9, an IDU 300 includes a first pair of tabs $376_a$ movable on a first plane and a second pair of tabs $376_b$ movable on a second plane, wherein tabs $376_b$ are disposed radially outward of tabs $376_a$. Each of the first and second pair of tabs $376_{a,b}$ includes first and second portions (not shown) configured to secure barrier membrane 106. With reference to FIG. 10, a sterile barrier assembly 400 includes four tabs 476 movably arranged in a co-planar relation. Each tab 476 includes first and second portions (not shown) configured to secure barrier membrane 106 therebetween.

Figure 11:
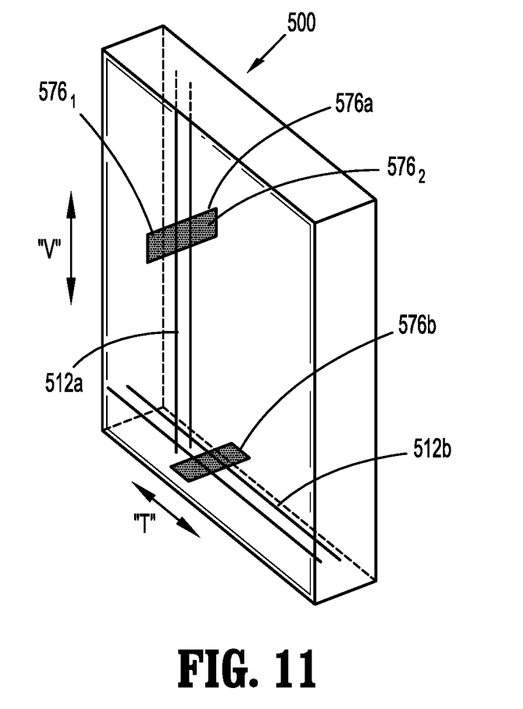

With reference now to FIG. 11, it is also contemplated that an IDU 500 may include actuation rails $512_{a,b}$ arranged in a non-parallel orientation and tabs $576_{a,b}$ operatively mounted on the respective actuation rails $512_{a,b}$. In particular, actuation rails $512_{a,b}$ may be transverse to each other such that tab $576_a$ is movable in the direction of an arrow "V" and tab $576_b$ is movable in the direction of arrow "T". Each tab $576_{a,b}$ includes first and second portions $576_{1,2}$. As discussed hereinabove, barrier membrane 106 may be interposed between first and second portions $576_{1,2}$ of tabs $576a,b$ to establish a hermetic seal between a sterile portion of a surgical instrument and a non-sterile portion of a manipulator assembly.

Figure 12:
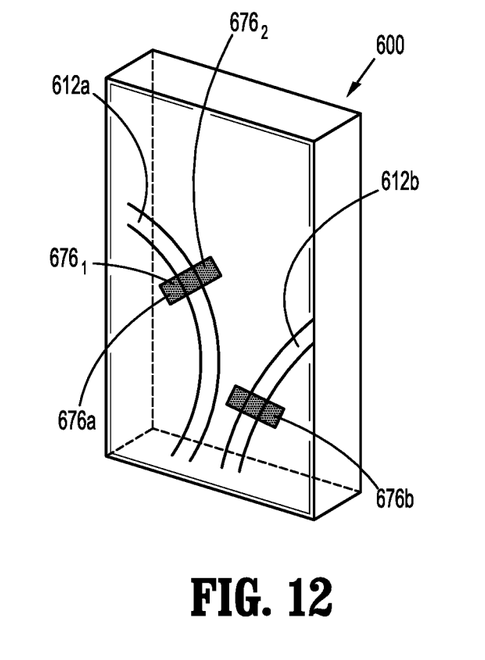

With reference now to FIG. 12, it is also contemplated that an IDU 600 may include actuation rails $612_{a,b}$ that are non-linear and tabs $676_{a,b}$ operatively mounted on the respective actuation rails $612_{a,b}$. Each actuation rail $612_{a,b}$ may define a radius of curvature tailored to meet the needs of the surgical instrument. Each tab $676_{a,b}$ includes first and second portions $676_{1,2}$. As discussed hereinabove, barrier membrane 106 may be interposed between first and second portions $676_{1,2}$ of tabs $676_{a,b}$ to establish a hermetic seal between a sterile portion of a surgical instrument and a non-sterile portion of a manipulator assembly.

Figure 13:
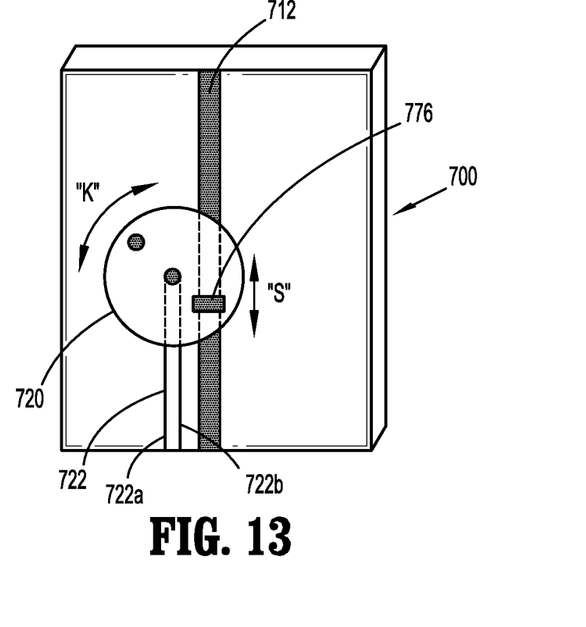

With reference now to FIG. 13, it is also contemplated that an IDU 700 may include an actuation rail 712 movable in the direction of an arrow "S", a tab 776 operatively mounted on actuation rail 712, a rotatable member 720 operatively coupled with tab 776, and a cable member 722 operatively associated with rotatable member 720. Tab 776 includes first and second portions (not shown). The first portion of tab 776 is operatively coupled with actuation rail 712, and the second portion of tab 776 is operatively coupled with rotatable member 720. Under such a configuration, movement of actuation rail 712 in the direction of arrow "S" causes rotation of rotatable member 720 in the direction of an arrow "K". Cable 722 is operatively coupled with rotatable member 720 such that rotation of rotatable member 720 causes movement of first and second ends $722_{a,b}$ of cable 722 in opposite directions. Barrier membrane 106 may be interposed between the first and second portions of tab 776 to establish a hermetic seal between a sterile portion of a surgical instrument and a non-sterile portion of a manipulator assembly.

Figure 14:
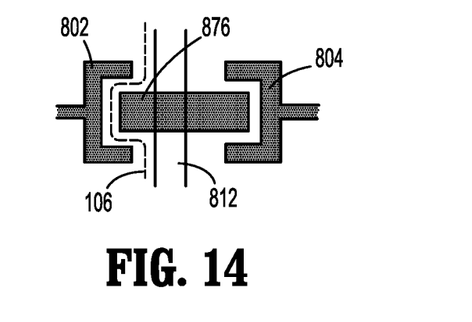
FIGS. 14 and 15 are partial side views of an instrument drive unit illustrating various barrier membrane arrangements.
Figure 15:
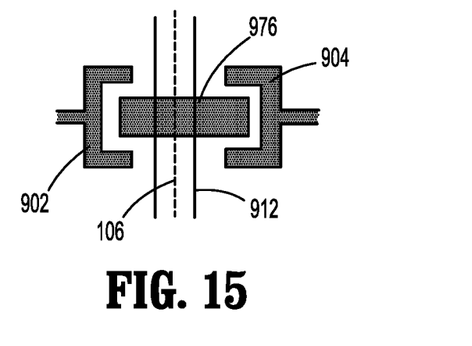

With reference now to FIG. 14, it is also envisioned that barrier membrane 106 may surround a tab 876 such that at least a portion of barrier membrane 106 is interposed between tab 876 and an interfacing member 802 of a surgical instrument such that barrier membrane 106 establishes a hermetic seal between a sterile portion of the surgical instrument and a non-sterile portion of a manipulator assembly and tab 876. Alternatively, it is also envisioned that at least a portion of barrier membrane 106 may be interposed between tab 876 and an interfacing member 804 of the manipulator assembly such that barrier membrane 106 establishes a hermetic seal between the sterile portion of the surgical instrument and tab 876, and the non-sterile portion of the manipulator assembly. In some instances, extra barrier membrane 106 may be provided to create slack in barrier membrane 106 to inhibit damage to barrier membrane 106 and undesirable pulling force applied to tab 876 by barrier membrane 106. Alternatively, barrier membrane 106 may be secured within an actuation rail 912 (FIG. 15) and a tab 976 (FIG. 15) such that barrier membrane 106 establishes a hermetic seal between an interfacing member 902 of a surgical instrument that is sterile and an interfacing member 904 of a manipulator assembly that is non-sterile.

While preferred embodiments of the present invention have been shown and described herein, it will be obvious to those skilled in the art that these embodiments are provided by way of example only. Numerous variations, changes, and substitutions will now occur to those skilled in the art without departing from the invention. Accordingly, it is intended that the invention be limited only by the spirit and scope of the appended claims.

Although the illustrative embodiments of the present disclosure have been described herein with reference to the accompanying drawings, the above description, disclosure, and figures should not be construed as limiting, but merely as exemplifications of particular embodiments. While sterile barrier assembly 100 has been shown for use with tabs $176_{1-4}$ configured for linear movement, it is also contemplated that sterile barrier assembly 100 may be tailored for use with tabs configured to transmit linear and rotary motion in all six degrees of freedom in one or multiple directions. It is to be understood, therefore, that the disclosure is not limited to those precise embodiments, and that various other changes and modifications may be effected therein by one skilled in the art without departing from the scope or spirit of the disclosure.

What is claimed is:

1. A sterile barrier assembly comprising:
 a tab sliding along a sliding path in a cavity of the sterile barrier assembly; and
 a barrier membrane partitioning the cavity into a sterile side and a non-sterile side, the barrier membrane at least partially moving with the tab as the tab slides along the sliding path, at least a portion of the barrier membrane disposed within the cavity of the sterile barrier assembly,
 wherein the sliding path extends between opposing outermost portions of the barrier membrane that are fixed such that a first portion of the tab interfaces with an output of a surgical tool driving unit on the non-sterile side, and a second portion of the tab interfaces with a tool driver of a surgical tool on the sterile side, wherein the barrier membrane is interposed between the first and the second portions of the tab such that at least a portion of the barrier membrane is securely movable with the first and second portions of the tab while providing a hermetic seal between the sterile side and the non-sterile side.

2. The sterile barrier assembly according to claim 1, wherein the barrier membrane is adjacent the first portion of the tab and the barrier membrane contours around at least one of the first portion of the tab and the output of the surgical tool driving unit as the first portion of the tab interfaces with the output of the surgical tool driving unit.

3. The sterile barrier assembly according to claim 1, wherein the barrier membrane is adjacent the second portion of the tab and the barrier membrane contours around at least one of the second portion of the tab and the tool driver as the second portion of the tab interfaces with the tool driver.

4. The sterile barrier assembly according to claim 3, wherein the output of the surgical tool driving unit moves rotationally while the tab and the tool driver move translationally and the tab imparts translational movement to the tool driver from the rotational output of the surgical tool driving unit.

5. The sterile barrier assembly according to claim 1, further comprising an elongated element attached to the tab and extending into a longitudinal channel in the sterile barrier assembly, the tab and elongated element sliding in a longitudinal direction of the channel.

6. The sterile barrier assembly according to claim 1, wherein the tab slides longitudinally along a guide rail in the sterile barrier assembly.

7. The sterile barrier assembly according to claim 1, wherein the barrier membrane is formed of an elastic material.

8. The sterile barrier assembly according to claim 1, wherein the barrier membrane is formed of an inelastic material.

9. The sterile barrier assembly according to claim 8, wherein the barrier membrane includes slack in the inelastic material that tautens as the tab slides in at least one direction.

10. The sterile barrier assembly according to claim 1, wherein the sliding path of the tab is coplanar with the barrier membrane.

* * * * *